United States Patent [19]
Burton

[11] Patent Number: 4,613,642
[45] Date of Patent: Sep. 23, 1986

[54] THERMALLY STABLE PHENOLIC COMPOUNDS

[75] Inventor: Lester P. J. Burton, Baton Rouge, La.

[73] Assignee: Ethyl Corporation, Richmond, Va.

[21] Appl. No.: 685,987

[22] Filed: Dec. 24, 1984

[51] Int. Cl.$^4$ .................. C07C 39/15; C08K 5/13
[52] U.S. Cl. ....................... 524/349; 568/744
[58] Field of Search ............ 524/101, 248, 291, 131, 524/150, 152, 141, 330, 339, 341, 342, 343, 344, 347, 349; 568/47, 48, 718, 720, 730, 744, 745, 323; 560/67, 75; 260/953

[56] References Cited

U.S. PATENT DOCUMENTS

| | | | |
|---|---|---|---|
| 2,285,626 | 6/1942 | Taylor et al. | 568/744 |
| 2,900,362 | 8/1959 | Spacht | 568/744 |
| 3,190,852 | 6/1965 | Doyle | 524/304 |
| 3,196,185 | 7/1965 | Ranson et al. | 524/342 |
| 3,255,255 | 6/1966 | Orloff | 568/720 |
| 3,257,321 | 6/1966 | Odenweller | 524/333 |
| 3,285,855 | 11/1966 | Dexter et al. | 524/291 |
| 3,297,575 | 1/1967 | Worrel | 568/720 |
| 3,531,483 | 9/1970 | Gilles | 524/101 |
| 3,532,669 | 10/1970 | Hunter | 524/150 |
| 3,553,270 | 1/1971 | Wollensak et al. | 524/330 |
| 3,562,338 | 2/1971 | Zaweski | 568/730 |
| 3,652,679 | 3/1972 | Zaweski | 524/333 |
| 3,678,047 | 7/1972 | Kletecka et al. | 524/101 |
| 3,717,610 | 2/1973 | Meltsner | 524/141 |
| 3,763,287 | 10/1973 | Chiddix et al. | 524/141 |
| 3,796,685 | 3/1974 | Brindell et al. | 524/333 |
| 3,816,544 | 6/1974 | Brindell et al. | . |
| 3,823,115 | 7/1974 | Brindell et al. | . |
| 3,824,192 | 7/1974 | Di Battista et al. | 524/131 |
| 3,836,590 | 9/1974 | Brindell et al. | . |
| 3,883,601 | 5/1975 | Brindell et al. | . |
| 3,944,594 | 3/1976 | Kleiner et al. | 524/291 |
| 4,038,327 | 7/1977 | Brindell | 568/745 |
| 4,082,808 | 4/1978 | Hay | 568/48 |

FOREIGN PATENT DOCUMENTS 825516 2/1960 U.S.S.R. .

*Primary Examiner*—Veronica P. Hoke
*Attorney, Agent, or Firm*—Donald L. Johnson; John F. Sieberth; Joseph D. Odenweller

[57] ABSTRACT

Compounds with 3,5-dibenzyl-4-hydroxyphenyl substituents have good thermal stability. Organic compositions containing the new additives are protected from oxidative degradation.

4 Claims, No Drawings

THERMALLY STABLE PHENOLIC COMPOUNDS

BACKGROUND OF THE INVENTION

This invention relates to aromatic phenolic compounds in general and in particular to compounds having a phenolic moiety with both positions ortho to the hydroxyl group substituted by benzyl substituents. Various materials, especially phenols have been suggested for use as antioxidants and for other stabilizing purposes in organic materials. There exists a need for phenolic materials which stabilize organic materials during processing as well as over extended storage periods.

SUMMARY OF THE INVENTION

The present invention is a new class of compounds and the stabilizer use of such compounds in organic materials. The invention includes organic material normally susceptible to gradual degradation in the presence of oxygen containing an antioxidant amount of a compound which includes in its structure the antioxidant function diorthobenzylphenol wherein said function is substituted at its para position with other than hydrogen or the 3,5-dibenzyl-4-hydroxybenzyl radical. The invention is also a class of compounds having the structure

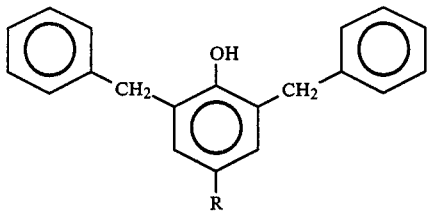

wherein R is not H and is an organic group other than the 3,5-dibenzyl-4-hydroxybenzyl radical.

The compounds of the present invention are valuable in comparison to presently available antioxidants having substituents ortho to the hydroxyl group other than benzyl because the compounds of the present invention are more thermally stable and provide additional protection to substrates during high temperature and other processing. Generally, the benzyl substituted compounds of the present invention are more thermally stable than their butylated counterparts. They exhibit a modest advantage when tested neat or in a substrate of organic materials such as polymers or other hydrocarbons.

DESCRIPTION OF THE PREFERRED EMBODIMENTS

The present invention is organic material normally susceptible to gradual degradation in the presence of oxygen containing an antioxidant amount of a compound selected from the group consisting of those compounds having the following structures:

A—S—R;
A—R'—O—R;
A—R'—S—R;
$(A-R')_{\overline{n}}-N+R)_{3-n}$;

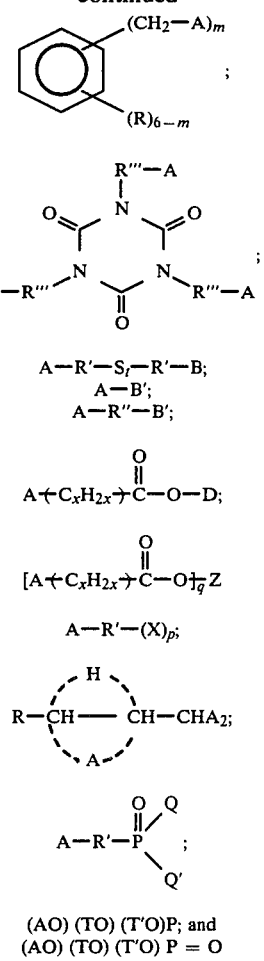

A—R'—S$_t$—R'—B;
A—B';
A—R''—B';

$$A+C_xH_{2x}+\overset{O}{\underset{\|}{C}}-O-D;$$

$$[A+C_xH_{2x}+\overset{O}{\underset{\|}{C}}-O+_qZ$$

A—R'—(X)$_p$;

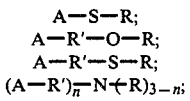

$$A-R'-\overset{O}{\underset{\|}{P}}\diagup^{Q}_{Q'}\ ;$$

(AO) (TO) (T'O)P; and
(AO) (TO) (T'O) P = O

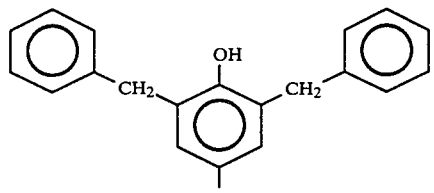

R is hydrogen, monovalent alkyl, aryl, alkaryl, aralkyl or A;
R' is divalent alkylene or alkylidene;
R" is divalent alkylene, alkylidene, or arylene of two or more carbon atoms.
R'" is divalent alkylene, a single bond or the group

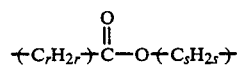

wherein
r is an integer from 0 to 8, s is an integer from 1 to 12 and A is bonded to the $+C_rH_{2r}+$ group;
B is A or hydrogen;
B' is A or an alkylphenol;
n is 1 to 3;
m is 1 to 3;
p is 1 or more;
D is hydrogen or alkyl;
X is halogen;

Q and Q' are alkoxy, phenoxy, alkylphenoxy, or alkylthio;

T and T' are A, alkylphenyl, dialkylphenyl, hydroxyalkylphenyl or hydroxydialkylphenyl;

x is 0 to 6;

q is 2 to 6;

t is 1 to 3;

Z is a polyvalent aliphatic hydrocarbon of formula $C_yH_{2y+2-q}$ where y is 2 to 18 when q is 2 and y is 3 to 6 when q is greater than 2.

The present invention is also an antioxidant compound of high thermal stability said compound being selected from the group consisting of those compounds having the following structures:

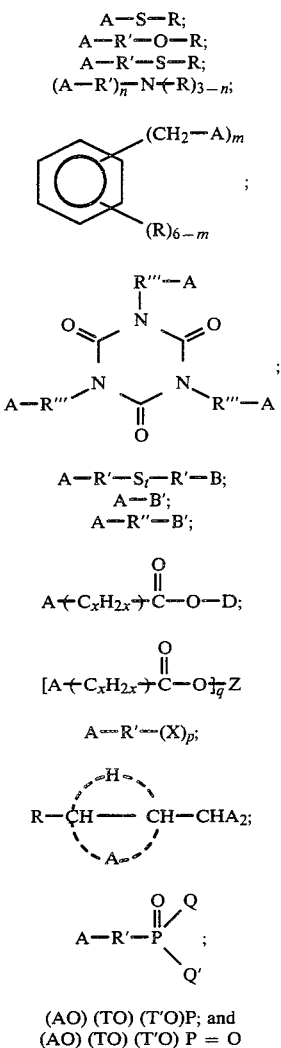

R is hydrogen, monovalent alkyl, aryl, alkaryl, aralkyl or A;

R' is divalent alkylene or alkylidene;

R'' is divalent alkylene, alkylidene, or arylene of two or more carbon atoms.

R''' is divalent alkylene, a single bond or the group

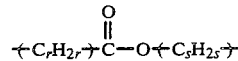

wherein r is an integer from 0 to 8, s is an integer from 1 to 12 and A is bonded to the $-(C_rH_{2r})-$ group;

B is A or hydrogen;

B' is A or an alkylphenol;

n is 1 to 3;

m is 1 to 3;

p is 1 or more;

D is hydrogen or alkyl;

X is halogen;

Q and Q' are alkoxy, phenoxy, alkylphenoxy, or alkylthio;

T and T' are A, alkylphenyl, dialkylphenyl, hydroxyalkylphenyl or hydroxydialkylphenyl;

x is 0 to 6;

q is 2 to 6;

t is 1 to 3;

Z is a polyvalent aliphatic hydrocarbon of formula $C_yH_{2y+2-q}$ where y is 2 to 18 when q is 2 and y is 3 to 6 when q is greater than 2.

A preferred embodiment of the present invention is organic material normally susceptible to degradation in the presence of oxygen and containing an antioxidant amount of one of the compounds of the invention. These novel compounds all include in their structure an antioxidant function whose structure is 3,5-dibenzyl-4-hydroxyphenyl which is substituted at its para position with an organic radical other than the 3,5-dibenzyl-4-hydroxybenzyl radical.

The compounds may be prepared by known methods. The starting material of the compounds of the invention are usually 2,6-dibenzylphenol or a substituted analog thereof. Of course, the 4 position of the 2,6-dibenzylphenol must be either unsubstituted or substituted in such a manner that it is available for replacement or further substitution to accommodate formation of the compounds of the invention.

The compounds of the preferred embodiments of the present invention include those in the classes discussed below. The various classes discussed herein may be represented structurally as given below wherein the monovalent 2,6-dibenzylphenol moiety bonded at its 4 position is represented by "A".

I. The compounds of the invention include 4-thiol substituted 2,6-dibenzylphenol and the related thioether compounds including those wherein the other moiety of the ether is an alkyl, aryl, alkaryl, or aralkyl radical. Thus compounds of the following structures are within the invention:

A—S—R wherein A is the 3,5-dibenzyl-4-hydroxyphenyl radical which may have a substituent at the 2 or 6 position or both. R is hydrogen or any hydrocarbyl radical which may optionally be substituted. Typical compounds are those where R may be any of the following: methyl, ethyl, isopropyl, sec-butyl, tert-butyl, octyl, hydroxyethyl, nitropropyl, amino methyl, aralkoxy, butyl, phenyl, phenethyl, benzyl, hydroxyphenyl, naphthyl, or another moiety. Preferred are those compounds where R is an alkyl or aromatic hydrocarbon. R may also be a phenolic substituent including A. The compounds of this class of the invention may be prepared according to the process disclosed in U.S. Pat. No. 3,145,176, incorporated herein by reference. Examples of compounds in this class of the invention are:

2,6-dibenzyl-4-mercaptophenol
bis(3,5-dibenzyl-4-hydroxyphenyl) thioether
(3,5-dibenzyl-4-hydroxyphenyl) (3,5-di-tert-butyl-4-hydroxyphenyl) thioether A highly preferred compound is bis(3,5-dibenzyl-4-hydroxyphenyl) thioether.

II. Another class of compounds of the invention are those of the structure:

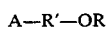

wherein R' is a divalent alkylene or alkylidene radical which may be methylene, ethylene, ethylidene, isopropylidene, and the like. Those compounds are preferred where R' is $C_1$ to $C_6$ alkylene. R may be hydrogen or hydrocarbyl; preferably alkyl, more preferably $C_1$-$C_6$ alkyl. Highly preferred are 2,6-dibenzyl-4-hydroxymethylphenol; 2,6-dibenzyl-4-(1-hydroxyethyl)phenol and the α-alkoxy-2,6-dibenzyl-p-cresols such as α-methoxy-2,6-dibenzyl-p-cresol; α-ethoxy-2,6-dibenzyl-p-cresol; α-butoxy-2,6-dibenzyl-p-cresol; α-isopropoxy-2,6-dibenzyl-p-cresol; α-n-decyloxy-2,6-dibenzyl-p-cresol; α-allyloxy-2,6-dibenzyl-p-cresol; α-(2-hydroxyethoxy)-2,6-dibenzyl-p-cresol and the like.

III. Another class of compounds of the invention are those of the structure:

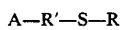

wherein R' is a divalent alkylene or alkylidene linkage and R is a monovalent alkyl, aryl, alkaryl, or aralkyl, optionally substituted. Preferred compounds of this class are 2,6-dibenzyl-alphaalkylthio-p-cresols. Examples of the compounds of this class are:

2,6-dibenzyl-α-methylthio-p-cresol
2,6-dibenzyl-α-ethylthio-p-cresol
2,6-dibenzyl-α-n-decylthio-p-cresol
α-allylthio-2,6-dibenzyl-p-cresol
2,6-dibenzyl-α-isopropylthio-p-cresol.

Such compounds may be prepared according to a procedure disclosed in U.S. Pat. No. 2,838,571, incorporated herein by reference.

IV. Also included in the invention are the 3,5-dibenzyl-4-hydroxyphenyl compounds having an amino hydrocarbyl substituent as in the following structure:

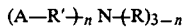

wherein n=1, 2, or 3 and R' may be any suitable divalent hydrocarbyl bridge. The R are the same or different monovalent hydrocarbyl radicals optionally substituted. Examples of this class of compounds are 2,6-dibenzylphenols substituted at the 4 position by dimethylaminomethyl, di(hydroxyethyl)aminomethyl, diethylaminobutyl, dimethylaminopropyl and the like. Other compounds of this class include tris(3,5-dibenzyl-4-hydroxybenzyl) amine; N,N-bis-(3,5-dibenzyl-4-hydroxybenzyl) octadecylamine and the like. Preferred are the compounds where n is one, R' is methylene, and the R's are the same or different alkyl, more preferably lower alkyl, for example α-dimethylamino-2,6-dibenzyl-p-cresol.

The compounds of this class may be prepared according to the method disclosed in U.S. Pat. No. 2,962,531, incorporated herein by reference. Other examples of the compounds of this class are:

2,6-dibenzyl-α-di(hydroxymethyl)amino-p-cresol
α,α'-(methylimino)bis(2,6-dibenzyl-p-cresol).

Most preferred is 2,6-dibenzyl-α-dimethylamino-p-cresol.

V. Another class of compounds of the invention are the benzenes which have at least one 2,6-dibenzylphenol as a substituent attached at its 4 position through an alkylene, preferably methylene, group and optionally having alkyl, aryl, or other substituents preferably methyl substituents on the benzene ring according to the following structure:

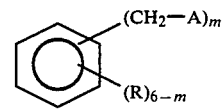

wherein the R's are the same or different and are hydrogen or a monovalent hydrocarbyl radical containing 1-20 carbon atoms or other stable substituent, preferably methyl and m is 1 to 3.

The preferred members of this class are those where R is represented by hydrogen and alkyls such as methyl, ethyl, or the like, preferably methyl; that is alkyl substituted benzenes wherein at least one 3,5-dibenzyl-4-hydroxybenzyl substituent is also attached to the benzene ring. More preferred are those compounds wherein the substituents are methyl and still more preferred are those compounds wherein more than one 3,5-dibenzyl-4-hydroxybenzyl substituent is attached to the benzene ring. Examples of compounds of this class include:

1,4-bis(3,5-dibenzyl-4-hydroxybenzyl)durene;
1,4-bis(3,5-dibenzyl-4-hydroxybenzyl)-2,3,5,6-tetraethylbenzene;
1-(3,5-dibenzyl-4-hydroxybenzyl)-2,4,6-trimethylbenzene;
1,3,5-tris(3,5-dibenzyl-4-hydroxybenzyl)-2,4,6-triethylbenzene;
1,3,5-tris(3,5-dibenzyl-4-hydroxybenzyl)-2,4,6-tri-sec-butylbenzene;
1,4-bis(3,5-dibenzyl-4-hydroxybenzyl)-2,5-dimethyl-3,6-dieicosylbenzene and the like. The most preferred compound in this class is 1,3,5-trimethyl-2,4,6-tris(3,5-dibenzyl-4-hydroxybenzyl)benzene.

VI. Another class of the invention are the isocyanurate compounds having 2,6-dibenzylphenol substituents attached at its 4 position to a nitrogen of the isocyanurate ring such as compounds having the following structure:

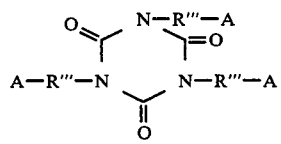

wherein R''' is a single bond, divalent alkylene, or the group

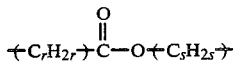

wherein r is an integer from 0 to 8, s is an integer from 1 to 12 and A is bonded to the $+C_rH_{2r}+$ group.

Representative examples of these compounds are:
2,2',2"-tris[3-(3,5-dibenzyl-4-hydroxyphenyl) propionyloxy]-N,N',N"-triethylisocyanurate;
2,2',2"-tris[2-(3,5-dibenzyl-4-hydroxyphenyl)acetyloxy]-N,N',N"-triethylisocyanurate;
2,2',2"-tris[4-(3,5-dibenzyl-4-hydroxyphenyl)butyryloxy]-N,N',N"-triethylisocyanurate;
3,3',3"-tris 6-(3,5,-dibenzyl-4-hydroxyphenyl)hexanoyloxy]-N,N',N"-tripropylisocyanurate;
2,2',2"-tris(3,5-dibenzyl-4-hydroxyphenylcarboxyl)-N,N',N"-triethylisocyanurate;
2,2',2"-tris(3,5-dibenzyl-4-hydroxyphenyl)-N,N',N"-triethylisocyanurate;
3,3',3"-tris(3,5-dibenzyl-4-hydroxyphenyl)-N,N',N"-tripropylisocyanurate;
4,4',4"-tris(3,5-dibenzyl-4-hydroxyphenyl)-N,N',N"-tributylisocyanurate;
and the like.

Preferred among such compounds in this class are 1,3,5-tris(3,5-dibenzyl-4-hydroxybenzyl)isocyanurate and 2,2',2"-tris-[3-(3,5-dibenzyl-4-hydroxyphenyl)propionyloxy]-N,N',N"-triethylisocyanurate. Such compounds may be prepared according to the disclosure of U.S. Pat. Nos. 3,531,483 and 3,678,047, incorporated herein by reference.

VII. A further class of compounds according to the invention are those of the structure

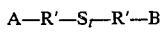

wherein B is hydrogen or A and t is an integer from 1 to 3. The R's may be the same or different and are divalent hydrocarbyl groups such as methylene, ethylidene, ethylene, isopropylidene, phenylene, or substituted hydrocarbyl groups. Representative examples of this class of compounds include β,β'-thiobis(2,6-dibenzyl-4-ethylphenol); α,α'-thiobis(2,6-dibenzyl-4-propylphenol); 3,5-dibenzyl-4-hydroxybenzyl mercaptan; 3,5-dibenzyl-4-hydroxyphenethyl mercaptan; α,α'-dithiobis(2,6-dibenzyl-p-cresol); β,β'-trithiobis(2,6-dibenzyl-4-ethylphenol) and the like. A preferred compound in this class of compounds is α,α'-thiobis(2,6-dibenzyl-p-cresol). These compounds may be prepared according to the procedure described in U.S. Pat. Nos. 3,065,275 and 3,272,869 incorporated herein by reference.

VIII. Another class of compounds according to the invention are those bicyclic compounds including biaryl compounds such as biphenols wherein a 2,6-dibenzyl group is bridged at its 4 position directly to another phenolic function represented in the following formula as B':

wherein B' is A, hydroxyphenyl, or an alkyl substituted hydroxyphenyl. The preferred compounds of this class are those wherein the 2,6-dibenzylphenol function is bonded at its 4 position to another phenol, most preferably another 2,6-dibenzylphenol moiety bonded at the 4 position. This class of compounds may be prepared according to procedures disclosed in U.S. Pat. Nos. 3,562,338; 3,631,208; 4,205,187; 4,238,627; 4,397,785 and 4,447,656, incorporated herein by reference. Compounds of this class are:
4,4'-bis(2,6-dibenzyl biphenol);
2,6-dibenzyl-4-(3,5-di-tert-butyl-4-hydroxyphenyl)-phenol;
2,6-dibenzyl-4-(3-sec-butyl-4-hydroxyphenyl)phenol;
2,6-dibenzyl-4-(3,5-diethyl-4-hydroxyphenyl)phenol;
2,6-dibenzyl-4-(4-hydroxyphenyl)phenol and the like.

IX. Another class of compounds according to the invention are the biphenols according to the following structure

wherein R" is a $C_2$ or higher divalent hydrocarbyl radical such as $C_2$ or higher alkylene, alkylidene, arylene, or the like and B' is A, hydroxyphenyl, or an alkyl substituted hydroxyphenyl. A preferred class are the alkylidene bridges; i.e., wherein R' is isopropylidene, ethylidene, and the like. A preferred compound of this invention is 4,4'-isopropylidenebis(2,6-dibenzylphenol). Such compounds may be prepared according to the method disclosed in U.S. Pat. No. 3,367,980, incorporated herein by reference. Compounds of this class of the invention also include:
4,4'-ethylidenebis(2,6-dibenzylphenol);
2-(3,5-dibenzyl-4-hydroxyphenyl)-2-(3,5-di-tert-butyl-4-hydroxyphenyl)propane; and
1-(3,5-dibenzyl-4-hydroxyphenyl)-1-(4-hydroxyphenyl)ethane.

X. Another class of compounds according to the invention are those wherein the 2,6-dibenzylphenol function is bridged at its 4 position to a carbon atom in an alkyl ester according to the following structure

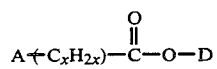

wherein D is an alkyl having 1 to 30 carbon atoms or hydrogen and x is 0 to 6. Representative examples of these compounds are:
2-(3,5-dibenzyl-4-hydroxyphenyl)acetic acid;
3-(3,5-dibenzyl-4-hydroxyphenyl)propionic acid;
4-(3,5-dibenzyl-4-hydroxyphenyl)butyric acid;
methyl 2-(3,5-dibenzyl-4-hydroxyphenyl)acetate;
ethyl 2-(3,5-dibenzyl-4-hydroxyphenyl)acetate;
2-ethylhexyl 3-(3,5-dibenzyl-4-hydroxyphenyl)propionate;
n-dodecyl 4-(3,5-dibenzyl-4-hydroxyphenyl)butyrate;
sec-eicosyl 6-(3,5-dibenzyl-4-hydroxyphenyl)hexanoate;
n-octadecyl 5-(3,5-dibenzyl-4-hydroxyphenyl)valerate;
n-docosyl 3-(3,5-dibenzyl-4-hydroxyphenyl)propionate;
n-triacontyl 3-(3,5-dibenzyl-4-hydroxyphenyl)propionate;
and the like. A preferred group of compounds in this class of the invention are the propionate esters such as the alkyl 3-(3,5-dibenzyl-4-hydroxyphenyl)propionates. The most preferred compound in this class is the n-octadecyl 3-(3,5-dibenzyl-4-hydroxyphenyl)propionate. This class of compounds may be prepared according to the procedures described in the following U.S. Pat. Nos.: 3,364,250, 3,330,859 and 3,285,885, incorporated herein by reference. Newer techniques for preparation of these compounds are also available as disclosed in U.S. Pat. Nos. 4,228,297 and 4,085,132, also incorporated herein by reference.

XI. A subclass of compounds according to the invention are still other esters derived from (3,5-dibenzyl-4-hydroxyphenyl)alkanoic acids and alkane polyols according to

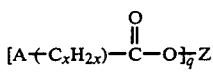

where x is 0 to 6, q is 2 to 6, and Z is a polyvalent aliphatic hydrocarbon of formula $C_yH_{2y+2-q}$ and y is 2 to 18 when q is 2 and y is 3 to 6 when q is greater than 2.

Conventional esterification techniques for their preparation are disclosed in U.S. Pat. No. 3,644,482. These compounds contain more than one (3,5-dibenzyl-4-hydroxyphenyl) alkanoic function on an alkane polyol structure. Exemplary of this class and most preferred is pentaerythritol tetrakis[3-(3,5-dibenzyl-4-hydroxyphenyl)propionate]. Other compounds of this class are ethylene glycol bis[3-(3,5-dibenzyl-4-hydroxyphenyl)propionate];

1,1,1-trimethylolethane tris[3-(3,5-dibenzyl-4-hydroxyphenyl)propionate];

glycerol tris[3-(3,5-dibenzyl-4-hydroxyphenyl)propionate];

1,4-pentane diol bis[2-(3,5-dibenzyl-4-hydroxyphenyl)acetate];

1,8-octane diol bis[4-(3,5-dibenzyl-4-hydroxyphenyl)butyrate];

1,6-hexane diol bis[7-(3,5-dibenzyl-4-hydroxyphenyl)heptanoate];

1,1,1-trimethylolpropane tris[3-(3,5-dibenzyl-4-hydroxyphenyl)propionate];

1,3-propane diol bis[2-(3,5-dibenzyl-4-hydroxyphenyl)acetate];

pentaerythritol tetrakis[2-(3,5-dibenzyl-4-hydroxyphenyl)acetate];

1,4-butane diol bis[3-(3,5-dibenzyl-4-hydroxyphenyl)propionate];

pentaerythritol tetrakis[6-(3,5-dibenzyl-4-hydroxyphenyl)hexanoate]

and the like.

XII. Another class of compounds of the invention are those halogenated compounds of the following structure:

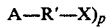

wherein R' is a lower divalent hydrocarbyl radical such as methylene, ethylidene, isopropylidene or the like where n is one or more and X is a halogen, especially chlorine or bromine. The 2,6-dibenzyl-4-halomethylphenols are preferred, especially 2,6-dibenzyl-4-chloromethylphenol (or 2,6-dibenzyl-alpha-chloro-p-cresol). Such compounds may be prepared according to the procedure of U.S. Pat. No. 3,257,321, incorporated herein by reference. Other compounds of this class are 2,6-dibenzyl-4-bromomethylphenol; 2,6-dibenzyl-4-(1-chloroethyl)phenol; 2,6-dibenzyl-4-(1-bromoisopropyl)phenol; 2,6-dibenzyl-4-(1-chloroisopropyl)phenol and the like.

XIII. Another class of compounds of the invention are the alkanes having three 2,6-dibenzylphenol substituents. Such compounds are generally formed according to a procedure described in U.S. Pat. No. 3,196,185, incorporated herein by reference. The compounds have the structure:

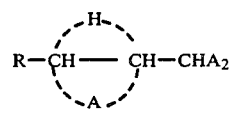

wherein R is hydrogen or a monovalent hydrocarbyl group. Preferably R is an alkyl containing 1 to 12 carbon atoms. The broken lines mean that A is bonded to one of the C atoms and H to the other. 2,6-dibenzylphenyl is reacted with an alpha-beta unsaturated aldehyde like crotonaldehyde to form, according to the invention, a 1,1,3-tris(3,5-dibenzyl-4-hydroxyphenyl)butane and/or 1,1,2-tris(3,5-dibenzyl-4-hydroxyphenyl)butane.

XIV. Another class of compounds of the invention are the phosphonates having a 2,6-dibenzylphenol attached through an alkylene group to a phosphorus atom also having attached thereto two hydrocarbyloxy substituents and an oxygen:

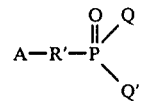

wherein R' is divalent alkylene, preferably methylene, and Q and Q' are selected from alkylphenoxy, alkoxy, phenoxy and alkylthio. Such compounds may be prepared by the preparation disclosed in U.S. Pat. No. 3,280,070, incorporated herein by reference.

Preferably the alkylene group contains 1–3 carbon atoms, the alkylphenoxy contains 7–12 carbon atoms, the alkoxy contains 1–30 carbon atoms and the alkylthio contains 1–30 carbon atoms. Representative examples of these compounds are O,O'-dimethyl (3,5-dibenzyl-4-hydroxybenzyl)phosphonate; O,O'-dibutyl (3,5-dibenzyl-4-hydroxybenzyl)phosphonate; O,O'-di-n-dodecyl (3,5-dibenzyl-4-hydroxybenzyl)phosphonate; O,O'-di-n-octadecyl (3,5-dibenzyl-4-hydroxy-α-methylbenzyl)phosphonate; O,O'-di-sec-eicosyl (-3,5-dibenzyl-4-hydroxy-α,α-dimethylbenzyl)phosphonate; O,O'-ditriacontyl (3,5-dibenzyl-4-hydroxybenzyl)phosphonate; O,O'-dihexadecyl (3,5-dibenzyl-4-hydroxybenzyl)phosphonate; O,O'-diphenyl (3,5-dibenzyl-4-hydroxybenzyl)phosphonate; O,O'-di-p-ethylphenyl (3,5-dibenzyl-4-hydroxybenzyl)phosphonate; O,O'-di-p-dodecylphenyl (3,5-dibenzyl-4-hydroxybenzyl)phosphonate; S,S'-dimethyl (3,5-dibenzyl-4-hydroxybenzyl)dithiophosphonate; S,S'-didodecyl (3,5-dibenzyl-4-hydroxybenzyl)dithiophosphonate; S,S'-dieicosyl (3,5-dibenzyl-4-hydroxybenzyl)dithiophosphonate and the like.

XV. Another class of the antioxidants of this invention are the phosphites and phosphates having the structures:

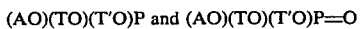

wherein T and T' are selected from the group consisting of A, and phenyl groups which may be substituted with alkyl, hydroxy, halo, alkoxy, other inert substituent or a combination of substituents such as an alkylhydroxyphenyl wherein the alkyls contain about 1–8 carbon atoms. Examples of these compounds are (3,5-dibenzyl-4-hydroxyphenyl) bis(3,5-di-tert-butyl-4-hydroxyphenyl) phosphite; bis(3,5-dibenzyl-4-hydroxyphenyl) (3,5-diisopropyl-4-hydroxyphenyl) phosphite; tris-(3,5-dibenzyl-4-hydroxyphenyl) phosphite; (3,5-dibenzyl-4- hydroxyphenyl) bis(3-tert-octyl-5-tert-butyl-4-hydroxyphenyl) phosphite; (3,5-dibenzyl-4-hydroxyphenyl) bis(2,6-diethylphenyl) phosphite; bis(3,5-dibenzyl-4-hydroxyphenyl) (2,6-di-tert-butylphenyl) phosphite and the corresponding phosphate compounds and the like.

In all of the above classes wherever the 3,5-dibenzyl-4-hydroxyphenyl moiety is present, the 2- and 6-positions of such moiety may be substituted with groups which permit stability of the compound. For example, the following groups may be substituted in the 2- and/or 6-positions (meta to the hydroxy) in all of the above compounds on the 3,5-dibenzyl-4-hydroxyphenyl ring: nitro, amino, halo, trihalomethyl, hydroxyalkyl, hydroxyaryl, alkoxy, hydroxy, aryloxy, thioalkyl, and others.

All of the above classes of compounds of the invention are usable either as stabilizers or as intermediates for preparation of other compounds containing the 3,5-dibenzyl-4-hydroxyphenyl function. For example the 3,5-dibenzyl-4-halomethyl compounds have a reactive halogen that will react with primary alcohols to introduce alkoxy substitution or with dialkylamines to form the dialkylaminomethyl substituent, both of which are good antioxidants. A particularly preferred stabilizer use is that of antioxidant and the compounds of the invention show great thermal stability for this and other uses.

The antioxidants of the invention can be used in a broad range of organic material normally susceptible to gradual degradation in the presence of oxygen during use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In general, the present additives are not flame retarding additives nor flame suppressing additives and the degradation protected against is not combustion but, rather, the gradual deterioration of the organic composition due to the effects of oxygen over an extended period of time. On the other hand, the compounds of the invention are susceptible to use for other stabilizing activities including protection from degradation by exposure to ultraviolet radiation or gamma radiation. Some of the compounds and classes of compounds of the invention may be suitable for use as a polymerization inhibitor to stabilize monomers.

Examples of organic materials in which the additives are useful include polymers, both homopolymers and copolymers, of olefinically unsaturated monomers, for example, polyolefins such as polyethylene, polypropylene, polybutadiene, and the like. Also, poly-halohydrocarbons such as polyvinyl chloride, polychloroprene, polyvinylidene chloride, polyfluoro olefins, and the like, are afforded stabilization. The additives provide antioxidant protection in natural and synthetic rubbers such as copolymers of olefinically unsaturated monomers including styrene-butadiene rubber (SBR rubber), ethylenepropylene copolymers, ethylene-propylenediene terpolymers such as the terpolymer of ethylene, propylene and cyclopentadiene or 1,4-cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrile-butadiene-styrene (ABS) resins are effectively stabilized. Ethylenevinyl acetate copolymers are protected, as are butenemethylacrylate copolymers. Nitrogen-containing polymers such as polyurethanes, nitrile rubber, and lauryl acrylate-vinyl-pyrrolidone copolymers are effectively stabilized. Adhesive compositions such as solutions of polychloroprene (neoprene) in toluene are protected.

Petroleum oils such as solvent-refined, midcontinent lubricating oil and Gulfcoast lubricating oils are effectively stabilized. In hydrocarbon lubricating oils, both mineral and synthetic, the present additives are particularly effective when used in combination with a zinc dihydrocarbyldithiophosphate, e.g. zinc dialkyldithiophosphate or zinc dialkaryldithiophosphate.

The antioxidants of the present invention may be used with mineral oils whether obtained by solvent refining, hydrotreating, hydrocracking, or another method. Thus the antioxidants of the present invention are suitable for combination with a mineral oil of lubricating viscosity which is derived from a lubricating oil produced by contacting a hydrocarbon feedstock with hydrogen preferably in the presence of catalyst effective to promote hydrocracking, at hydrocarbon hydrocracking conditions to produce an oil of lubricating viscosity having an increased viscosity index relative to the viscosity index of the hydrocarbon feedstock.

Typical applications of the antioxidant additives of this invention in oils include use in all motor oils, crankcase oil, turbine oil, diesel oil, industrial oil, hydraulic fluids and the like.

The antioxidant additives of the invention are also useful in fuels including, but not limited to gasoline, alcohol, and the like.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and other polyformaldehydes are also protected.

Linear polyesters such as phthalic anhydride-glycol condensates are given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with olefinically unsaturated monomers such as methylmethacrylates are also effectively stabilized.

The additives can be used to protect any of the many organic substrates to which an antioxidant is normally added. It can be used where economics permit to protect such substrates as asphalt, paper, fluorocarbons such as teflon, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethylsilicone lubricants, phosphate lubricants such as tricresylphosphate, and the like.

The additives are incorporated into the organic substrate in a small but effective amount so as to provide the required antioxidant protection. A useful range is from about 0.005 to about 10 weight percent, and a preferred range is from about 0.05 to 5 weight percent.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with the additive or with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cispolybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized. The following will serve to illustrate the manner in which the additives are blended with various organic substrates.

EXAMPLE 1

Preparation of 2,6-dibenzyl-4-hydroxymethylphenol

The desired alcohol was prepared by reaction of 2,6-dibenzylphenol with an equivalent of 37% aqueous solution of formaldehyde in ethanol. A solution of 6.85 grams of 2,6-dibenzylphenol in 5 mL ethanol was added to a solution of 1.65 grams 85% KOH in 5 mL ethanol and stirred for 30 minutes. About 1.91 mL of a 37% formalin solution was added dropwise at 25° C. and stirred overnight. The ethanol was removed from the purple solution by rotary evaporation and the residue was dissolved in methylene chloride, washed with saturated ammonium chloride solution and brine, and dried over sodium sulfate. Solvent removal provided 6.6 grams of a crude orange solid which was analyzed by gas chromatography as 4.1 grams starting material 2,6-dibenzylphenol and 2.2 grams 2,6-dibenzyl-4-hydroxymethylphenol (m.p. 116° C.).

Based upon recovered starting material, a 90% yield was calculated. Both H-nuclear magnetic resonance spectroscopy (H-NMR) and infrared spectroscopy (IR) confirm the structure.

EXAMPLE 2

Preparation of bis(3,5-dibenzyl-4-hydroxybenzyl) sulfide

The 2,6-dibenzyl-4-hydroxymethylphenol of Example 1, 304 milligrams and 730 milligrams sodium sulfide nonahydrate were heated to reflux in 6 mL methanol for 6 hours. The mixture was cooled and an additional 304 milligrams of the 2,6-dibenzyl-4-hydroxymethylphenol was added and the mixture refluxed overnight. The methanol was removed by rotary evaporation and the residue was dissolved in ethyl acetate, washed with saturated ammonium chloride solution and brine, and dried over sodium sulfate. Solvent evaporation provided 530 milligrams of an orange oil which was analyzed as 83% bis(3,5-dibenzyl-4-hydroxybenzyl) sulfide. Both H-NMR and mass spectroscopy support the structural identification.

EXAMPLE 3

Preparation of 1,3,5-tris(3,5-dibenzyl-4-hydroxybenzyl)isocyanurate

About 4.52 grams 2,6-dibenzylphenol in 1.6 mL water and 12.5 mL dimethyl formamide were heated to 40° C. To this solution was added 645 milligrams cyanuric acid, 1.57 grams paraformaldehyde, and 455 milligrams hexamethylenetetramine. The entire mixture was poured onto ice, extracted with chloroform, washed with water, and dried over sodium sulfate. The solvent was removed at 1 Torr and cooling yielded a glassy brown solid. Recrystallization was difficult and purity of the useable product was not good but analysis showed 37% of 1.8 grams to be the desired 1,3,5-tris(3,5-dibenzyl-4-hydroxybenzyl)isocyanurate (m.p. 75° C.). The structure was confirmed by H-NMR, mass spec (MS), and IR.

EXAMPLE 4

Preparation of 1,3,5-trimethyl-2,4,6-tris(3,5-dibenzyl-4-hydroxybenzyl)benzene

Under nitrogen, 13.7 grams 2,6-dibenzylphenol, 2.4 grams paraformaldehyde, and 0.5 mL 40% aqueous dimethylamine were combined in 20 mL methanol. The mixture was refluxed for 8 hours. The crude product was concentrated to 15.8 grams amber oil. The structure of the intermediate, 2,6-dibenzyl-4-(methoxymethyl) phenol, was confirmed by H-NMR and a sample purified by column chromatography had a DSC melting point of 62° C.

The crude intermediate, 15.5 grams, was combined with 1.7 mL mesitylene, 0.15 mL glacial acetic acid and 20 mL methylene chloride. The mixture was cooled to −0.5° C. prior to addition of 2.6 mL concentrated (97%) sulfuric acid dropwise over a 3 minute period. The temperature rose to 10° C. Thereafter the temperature was maintained at about 3° C. for 2 hours. The mixture was diluted with 25 mL ice water and the suspended solids were collected by filtration. The filtrate was extracted with methylene chloride which was then dried over magnesium sulfate and concentrated to an amber oil. High pressure liquid chromatography separated the crude to provide a 22% yield based on 2,6-dibenzylphenol of 1,3,5-trimethyl-2,4,6-tris(3,5-dibenzyl-4-hydroxybenzyl)benzene. The structure was confirmed by H-NMR and IR (m.p. 121° C.).

EXAMPLE 5

Preparation of 4,4'-isopropylidenebis(2,6-dibenzylphenol)

About 0.6 grams 2,2-dimethoxypropane and 2.7 grams 2,6-dibenzylphenol were combined in a flame-dried flask. Anhydrous HCl was bubbled through the mixture. After 8 hours, an additional 0.5 mL 2,2-dimethoxypropane was added and anhydrous HCl bubbled through the mixture for 1 minute. The black oil was stirred 65 hours and concentrated under vacuum to provide 3.1 grams.

About 0.16 grams of 4,4'-isopropylidenebis(2,6-dibenzylphenol) were identified by H-NMR and MS. This is a conversion of 15% based on reacted 2,6-dibenzylphenol and a yield of 37%.

EXAMPLE 6

Preparation of 2,6-dibenzyl-alpha-dimethylamino-p-cresol

Aqueous dimethylamine (40%), 3.9 grams and 5.5 grams 2,6-dibenzylphenol were combined in 15 mL isopropyl alcohol and cooled to about 7° C. A 3.0 gram portion of paraformaldehyde was added. The stirred slurry was allowed to warm to room temperature. After 1 hour, the slurry was heated to and maintained at reflux for 3 hours. About 25 mL of ethyl acetate was added; the organics were washed with 20 mL water and separated. A precipitate formed during the second water wash. The slurry was filtered and a second crop of solids was obtained from the filtrate. Vacuum drying of the product provided a total of 6.8 grams white solids with a melting point of 114°–116° C. The H-NMR confirmed the presence of 2,6-dibenzyl-alpha-dimethylamino-p-cresol. Recrystallization from heptane resulted in an 87% yield of off-white solids with a m.p. of 112°–114° C.

EXAMPLE 7

A thermogravometric analysis of several compounds of the invention and several commercial compounds (for comparison) was made by heating carefully weighed small portions of the compounds (less than 0.1 gram each) such that the temperature of the compounds were raised at the rate of 10° C. per minute from room temperature under nitrogen conditions. The temperature at which the onset of weight loss was detected was recorded. Also recorded were the temperatures at which 5% and 10% of weight loss occurred. The results are shown in Table I.

TABLE I

| Compound | WEIGHT LOSS TEMPERATURE | | |
|---|---|---|---|
| | Onset | 5% | 10% |
| 2,6-dibenzyl-4-hydroxymethylphenol (Example 1) | 185 | 235 | 245 |
| 2,6-di-tert-butyl-4-hydroxymethylphenol | 115 | 155 | 170 |
| 1,3,5-tris(3,5-dibenzyl-4-hydroxybenzyl)isocyanurate (Example 3) | 90 | 280 | 305 |
| 1,3,5-tris(3,5-di-tert-butyl-4-hydroxybenzyl)-isocyanurate | 90 | 350 | 370 |
| 1,3,5-trimethyl-2,4,6-tris(3,5-dibenzyl-4-hydroxybenzyl)benzene (Example 4) | 325 | 390 | 405 |
| 1,3,5-trimethyl-2,4,6-tris(3,5-di-tert-butyl-4-hydroxybenzyl)benzene | 300 | 365 | 380 |

TABLE I-continued

| Compound | WEIGHT LOSS TEMPERATURE | | |
|---|---|---|---|
| | Onset | 5% | 10% |

The high thermal stability of the compound of Examples 1, 3, and 4 are advantageous in protecting polymers and other organic materials which are subjected to high temperatures during manufacturing processes or other exposure. The relatively quicker weight loss of the compound of Example 3 was apparently due to the poor purity of the sample used in this particular test.

EXAMPLE 8

In all of the melt flow index testing described below about 1,000 parts per million of calcium stearate was used as an acid neutralizer and lubricating agent. The blended materials were pelletized under nitrogen on a twin screw mixer (Brabender) with a temperature profile: zone 1°–150° C., zones 2 and 3°–245° C.; screw speed 30 rpm. Then, multiple extrusions (5 passes) were run on the pellets on a single screw extruder (Brabender L/D 24:1) at 260° C. (500° F.). The stock temperature was 265° C. and the screw speed was 30 rpm in air atmosphere. The extruded strand was cooled by passing through a room temperature water bath. Water carry-over was minimized by an air knife that blew the excess water from the strand before it entered the pelletizer. Material from each pass was collected and melt flow index was determined on each sample with a Tinius Olsen extrusion plastometer according to ASTM method D-1238 condition -1 (230° C. -2160 gram load). Using the same samples a 50 mill sheet was pressed out at 375° F. and color was determined with a Hunter Lab optical sensor model D25.

Along with other examples, the 1,3,5-tris(3,5-dibenzyl-4-hydroxybenzyl)isocyanurate of Example 3 and the commercially available 1,3,5-tris(3,5-di-tert-4-hydroxybenzyl)isocyanurate were each tested for processing stability in Hercules Profax 6501 in a single screw extruder L/D 25:1 at 260° C. (500° F.) and 30 rpm's. The polypropylene powder was stabilized with 1,000 parts per million of each of the samples tested. The melt flow index according to ASTM 1238 condition L, gram/10 minute was determined after 1, 3, and 5 passes. The color-yellowness index according to ASTM D1925 was also determined after 1 and 3 or 5 passes. Each of the formulations also contained 1,000 parts per million of calcium stearate. The results are shown in Table II.

TABLE II

| | PROCESSING STABILITY | | | | | |
|---|---|---|---|---|---|---|
| | Melt Flow Index Extrusion Passes | | | Color-Yellowness Index Extrusion Passes | | |
| Stabilizer | 1 | 3 | 5 | 1 | 3 | 5 |
| Blank | 7.4 | 19 | — | 3.8 | 5.1 | — |
| 1,3,5-tris(3,5-dibenzyl-4-hydroxybenzyl)isocyanurate (Example 3) | 3.0 | 3.9 | 4.7 | 5.5 | — | 12.3 |
| 1,3,5-tris(3,5-di-tert-butyl-4-hydroxybenzyl)isocyanurate | 3.6 | 7.6 | 11.9 | 9.7 | — | 12.3 |
| 2,6-dibenzyl-4-hydroxymethylphenol (1,000 ppm) | 3 | 4 | 4.5 | 6.1 | — | 12.9 |

TABLE II-continued

PROCESSING STABILITY

| Stabilizer | Melt Flow Index Extrusion Passes | | | Color-Yellowness Index Extrusion Passes | | |
|---|---|---|---|---|---|---|
| | 1 | 3 | 5 | 1 | 3 | 5 |
| 2,6-di-tert-butyl-4-hydroxymethylphenol (1,000 ppm)(Example 1) | 2.8 | 3.8 | 4.1 | 4 | 8.1 | |
| 2,6-dibenzyl-4-methoxymethylphenol | 3.3 | 6 | 9.2 | — | — | — |
| 2,6-di-tert-butyl-4-methoxymethylphenol | 4.3 | 6.2 | 7.2 | — | — | — |
| 1,3,5-trimethyl-2,4,6-tris(3,5-dibenzyl-4-hydroxybenzyl)benzene* (Example 4) | 3.0 | 3.5 | 4.2 | 3.9 | — | 9.5 |
| 1,3,5-trimethyl-2,4,6-tris(3,5-di-tert-butyl-4-hydroxybenzyl)-benzene* | 3.6 | 7.6 | 11.8 | 3.8 | — | 5.8 |

*at only 500 ppm

The relatively poorer performance of the compound of Example 3 is likely due to an impure sample. However, it can be seen that the compounds of the invention are generally more stable or as stable for color and melt flow as certain comparative commercial compounds, when tested in polypropylene. Advantages become more apparent with testing in compounds processed at even higher temperatures.

EXAMPLE 9

The 2,6-dibenzyl-alpha-dimethylamino-p-cresol compound of Example 6 was tested for solubility in oil in an oxidation and corrosion test. A saturated solution (<1% by weight) of the compound was as effective in preventing corrosion and oxidation of the oil as a 1% solution of commercially available antioxidant which is a condensation product of formaldehyde and butylated phenols which are in turn taken from the bottoms stream of an alkylation process to make 2,6-di-tert-butylphenol. The saturated solution contained less than 0.5 weight percent of the compound of Example 6 and it was not quite as effective as a 0.5% oil solution of 2,6-di-tert-butyl-alpha-dimethylamino-p-cresol.

EXAMPLE 10

Certain of the compounds of the invention were tested for long term antioxidant protection by oven aging of a polypropylene containing a small sample of each of the additives. Each compound was dissolved or dispersed in a very small amount (1 cc) of methylene chloride and mixed with 50 grams of Hercules Profax ® 6501 polypropylene powder. This homogeneous mixture was dry blended with 450 grams of polypropylene in a plastic bag under nitrogen. The material was pressed into a 25 mil sheet and tested by oven aging at 150° C. in an air circulated oven. The formulations contained 0.1% of each of the antioxidant compounds.

A polypropylene 25 mil sheet containing no antioxidant and no distearylthiodipropionate (DSTDP) synergist failed at 3 hours in the oven aging test. A sheet containing only 2,6-dibenzyl-p-cresol failed at 24 hours. A comparable sheet containing the 2,6-dibenzyl-p-cresol and calcium stearate at 0.1 wt. % also failed at 24 hours. A polypropylene sample containing 0.1 wt. % 2,6-dibenzyl-p-cresol 0.25 wt. % DSTDP and 0.1% calcium stearate failed at 244 hours. A comparable sample without the calcium stearate did not fail until 432 hours. A polypropylene sample containing only 0.25% DSTDP failed at a little more than 216 hours.

Since certain delineations and variations of the invention are available other than those shown above in the description and examples of the invention, one may vary from the above description without departing from the scope or spirit of the invention as defined by the appended claims.

I claim:

1. Polyolefin normally susceptible to gradual degradation in the presence of oxygen containing about 0.005 to about 10 weight percent 1,3,5-trimethyl-2,4,6-tris(3,5-dibenzyl-4hydroxybenzyl)benzene.

2. A composition of claim 1 wherein said polyolefin is polypropylene or polyethylene.

3. A composition of claim 2 wherein said polyolefin is polypropylene.

4. An antioxidant compound of high thermal stability, namely 1,3,5-tris(3,5-dibenzyl-4-hydroxybenzyl)-2,4,6-trimethylbenzene.

* * * * *

UNITED STATES PATENT AND TRADEMARK OFFICE
CERTIFICATE OF CORRECTION

PATENT NO.   :   4,613,642

DATED        :   SEPTEMBER 23, 1986

INVENTOR(S)  :   LESTER P. J. BURTON

It is certified that error appears in the above-identified patent and that said Letters Patent is hereby corrected as shown below:

Column 2, line 39, should read -- wherein A is -- .

Column 3, line 57, should read -- wherein A is -- .

Column 7, line 14, reads "6-(3,5-", and should read -- [6-(3,5- -- .

Column 9, line 46, reads "A - R' - X)$_p$" and should read -- A - R' $($ X)$_p$ -- .

Column 18, line 37, reads "dibenzyl-4hydroxybenzyl)" and should read -- dibenzyl-4-hydroxybenzyl)-- .

Signed and Sealed this

Twenty-third Day of December, 1986

Attest:

DONALD J. QUIGG

Attesting Officer        Commissioner of Patents and Trademarks